United States Patent [19]

Perryman

[11] 3,988,931
[45] Nov. 2, 1976

[54] APPARATUS AND METHOD FOR MEASURING MUSCULAR STRENGTH OF LOWER HUMAN EXTREMITIES

[76] Inventor: John S. Perryman, 17 S. Point Terrace, Kinnelon, N.J. 07405

[22] Filed: May 8, 1975

[21] Appl. No.: 575,741

[52] U.S. Cl. .................. 73/379; 73/133 A
[51] Int. Cl.² .......................... G01L 5/02
[58] Field of Search .......... 73/379 R, 133 A, 133 R; 280/11.35 R, 11.35 T, 11.35 M, 11.35 Y

[56] References Cited
UNITED STATES PATENTS

| | | | |
|---|---|---|---|
| 2,680,967 | 6/1954 | Newman | 73/379 R |
| 3,489,122 | 1/1970 | Schweizer et al. | 280/11.35 R X |
| 3,517,640 | 6/1970 | Unger | 280/11.35 R X |
| 3,686,950 | 8/1972 | Salomon | 73/379 R |
| 3,764,155 | 10/1973 | Perryman | 280/11.35 Y X |
| 3,830,101 | 8/1974 | Frey | 73/133 A |
| 3,874,685 | 4/1975 | Von Besser | 280/11.35 T X |

*Primary Examiner*—Richard C. Queisser
*Assistant Examiner*—Daniel M. Yasich
*Attorney, Agent, or Firm*—Anthony F. Cuoco

[57] ABSTRACT

Measurement of the torsional and bending capabilities of the lower extremities of a human body is accomplished by applying torsional (twisting) and bending (pitching) forces to the lower extremities through the muscular strength of a subject and to the limit of significant pain or discomfort. Means are provided for measuring the applied forces to provide torsional and bending indices, and which indices may be correlated for a variety of purposes desired.

14 Claims, 7 Drawing Figures

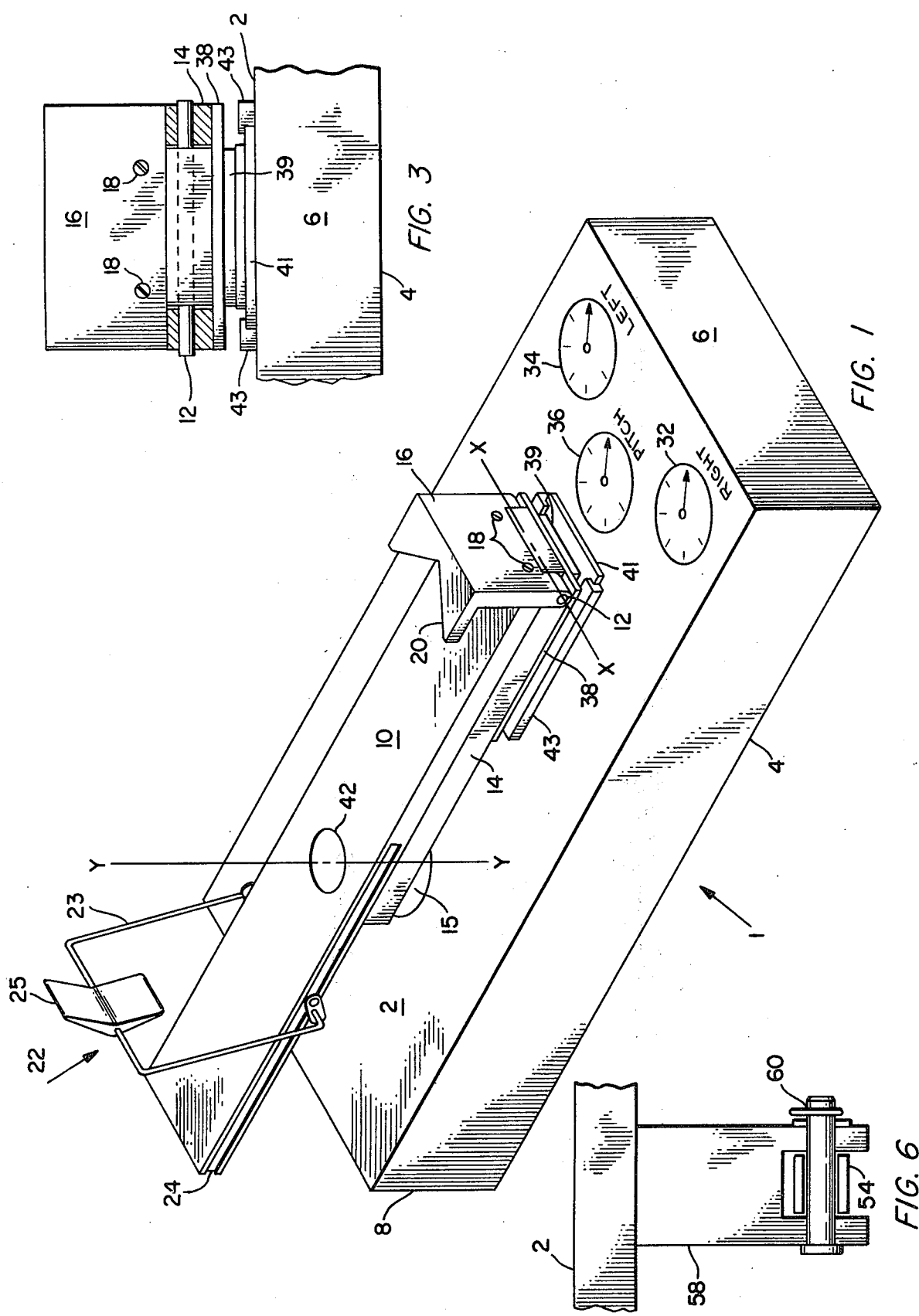

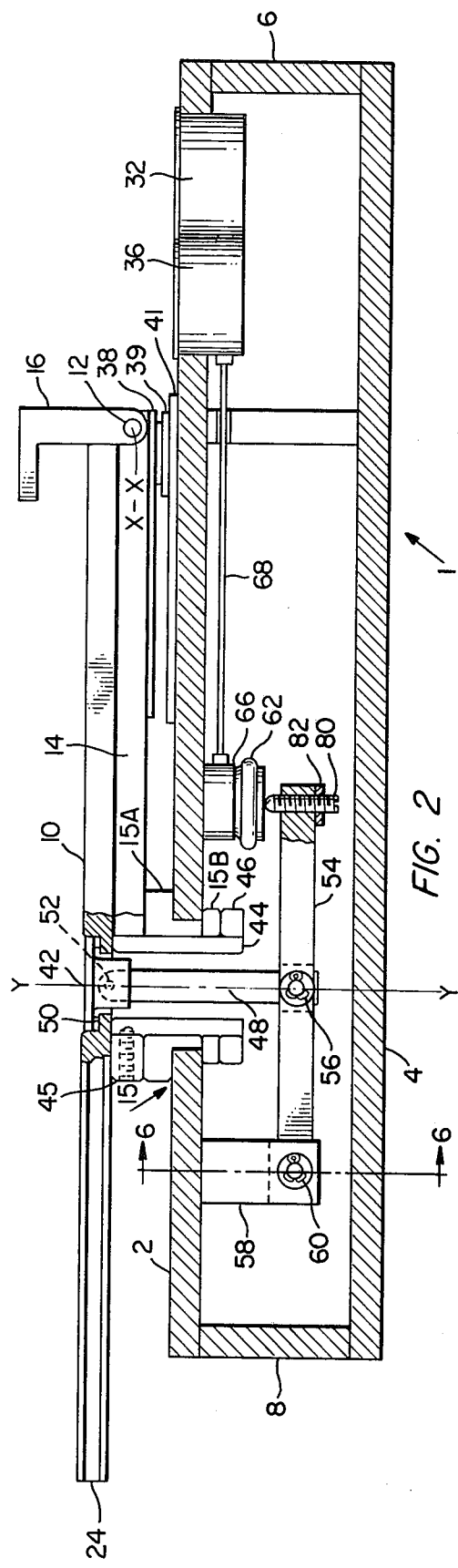

APPARATUS AND METHOD FOR MEASURING MUSCULAR STRENGTH OF LOWER HUMAN EXTREMITIES

BACKGROUND OF THE INVENTION

1. Field of the Invention

This invention relates generally to measuring the torsional and bending capabilities of the lower extremities of a human body and, particularly, to measuring said capabilities to the limit of significant pain or discomfort experienced by a subject in response to self-applied torsional and bending forces. More particularly, this invention relates to measurements of the type described which may be correlated or calibrated for a variety of purposes desired. Still more particularly this invention relates to measurements of the type described which may be calibrated for adjusting releaseable ski boot bindings whereby excessive torsional or bending forces experienced during, for example, a fall of a skier will release the skiers boot from the ski to reduce the risk of serious injury which might otherwise occur.

2. Description of the Prior Art

The sport of alpine skiing is such that releaseable ski boot bindings are in general acceptance to reduce the risk of injury to the skier which might occur during a fall or the like. A device for accomplishing this purpose is described in U.S. Pat. No. 3,764,155 issued on Oct. 9, 1973 to John S. Perryman, the inventor of the present invention, and which patent describes and claims a releaseable ski boot binding which will release the boot from the ski in response to excessive torsional and bending forces exerted upon the lower extremities of the skier. Likewise, U.S. Pat. No. 3,764,154 issued on Oct. 9, 1973 to Gerhard Whitting describes and claims a releaseable ski boot binding which reduces the boot from the ski when the retaining forces of the binding exceed given maximum values.

While the releasability of the ski bindings described in the aforenoted patents is adjustable, depending upon a variety of conditions, there has not heretofore been a means or method for adapting the adjustment to the capabilities of the individual skier. In most cases the adjustment is made utilizing general physical parameters such as weight, tibia bone diameter, sex, age, ability, skiing speed and such other factors as are discernable to those skilled in the art. The difficulty arises in the fact that the utilization of these parameters for the purposes intended is based on judgement (qualitative) rather than on measurement (quantitative). Accordingly, the results provided are relatively inaccurate and do not provide the maximum margin of safety while providing adequate ski binding retention for normal skiing. Typical of the prior art devices is that described and claimed in U.S. Pat. No. 3,389,472 issued on Dec. 6, 1966 to C. C. Lipe, et. al., wherein means are provided for adjusting the releaseability of the ski binding within a degree of safety consistent with the limits of the skiers ability, weight, age, physical condition and experience.

The prior art devices, however, do not take into account certain generally accepted facts that most healthy people will experience discomfort, pain, strain, sprain and then bone fracture, generally in that order, if undue loads are applied to their lower extremities as during a serious fall when skiing. It is also a generally accepted fact that a skier need not exert any more force for controlling his skis then he is physically able to apply within his own threshold of discomfort or pain.

The present invention recognizes that torsional and bending forces are the significant traumatic forces applied to the lower extremities of a skier for causing most injury producing accidents. Accordingly, the invention provides a means and method for measuring the torsional and bending capabilities of the lower extremities to the limit of significant discomfort and pain within the skiers individual threshold. The torsional and bending forces are applied through the skiers own muscular strength and measurements are achieved for his own individual capabilities, and which measurements may be used for adjusting ski binding releaseability or, in other words, used as ski binding retention indices.

SUMMARY OF THE INVENTION

This invention contemplates apparatus for the purposes described including a base plate, a pivot plate and a sole plate. The sole plate is hinged to the pivot plate to permit displacement of the sole plate about a transverse axis in response to forward or rearward bending forces applied to the lower extremities and the pivot plate is pivotally mounted to the base plate to permit displacement of the sole plate and pivot plate about an axis normal to the common plane of said plates in response to rightward or leftward torsional forces. Linkages are provided for transmitting the displacements to sensors, and which sensors are coupled to indicators for indicating the magnitude of the forces applied.

This invention further contemplates a method for using the apparatus described including the steps of clamping a suitably booted foot of a subject to the sole plate with the toe of the boot near the transverse axis, applying the forward bending force for displacing the sole plate about the transverse axis, sequentially applying the rightward and leftward torsional forces for displacing the sole plate and pivot plate about the normal axis, reversing the booted foot on the sole plate so that the boot is clamped with the heel near the transverse axis, applying the rearward bending force for displacing the sole plate about the transverse axis, and indicating the magnitude of the forces so applied. The indicated magnitudes of the applied forces may be correlated in accordance with a variety of purposes desired.

The main object of this invention is to provide a means and method for measuring the torsional (twisting) and bending (pitching) capabilities of the lower extremities of the human body within the threshold of discomfort or pain experienced by a subject.

Another object of this invention is to measure said capabilities by applying torsional and bending forces to the lower extremities, and to provide means responsive to the forces for indicating the magnitudes thereof, whereby indicies are provided for utilizing said indicated magnitudes for the purposes desired.

Another object of this invention is to measure said capabilities by self-application of the forces by the subject.

Another object of this invention is to provide calibration indices for the lower extremities of a subject, and which indices may be correlated for evaluating the muscular strength of the lower extremities.

Another object of this invention is to provide the aforenoted indices for adjusting the releaseability of releaseable ski bindings within the limits of the capabilities of the lower extremities of a skier to minimize the risk of injury upon a fall or the like while skiing.

Another object of this invention is to adjust the ski binding releaseability within the particular capabilities of the individual.

The aforegoing objects and advantages of the invention will appear more fully hereinafter from a consideration of the detailed description which follows taken together with the accompanying drawings wherein a single embodiment of the invention is illustrated by way of example. It is to be expressly understood, however, that the description of the invention and the drawings are for illustration purposes only and are not to be construed as defining the limits of the invention. For example, although the invention will be described as measuring the torsional and bending capabilities of the lower extremities of the human body as they may relate to the adjustment of releaseable ski bindings, or in other words to provide binding retention indicies, it will be understood that the invention may be used as well for the evaluation of healing or muscular development of the lower extremities as may be desired, for example, by practitioners of the medical arts.

DESCRIPTION OF THE DRAWINGS

FIG. 1 is an isometric pictorial representation showing the external features of the invention.

FIG. 2 is a partially sectioned side view, relative to FIG. 1, showing the internal mechanism of the invention.

FIG. 3 is a partially sectioned right end view, relative to FIG. 1, showing the external features of the invention.

FIG. 5 is a partial view of the invention taken along the line 5—5 in FIG. 4.

FIG. 6 is a view of the invention taken along the line 6—6 in FIG. 2.

DESCRIPTION OF THE INVENTION

Figure 4:
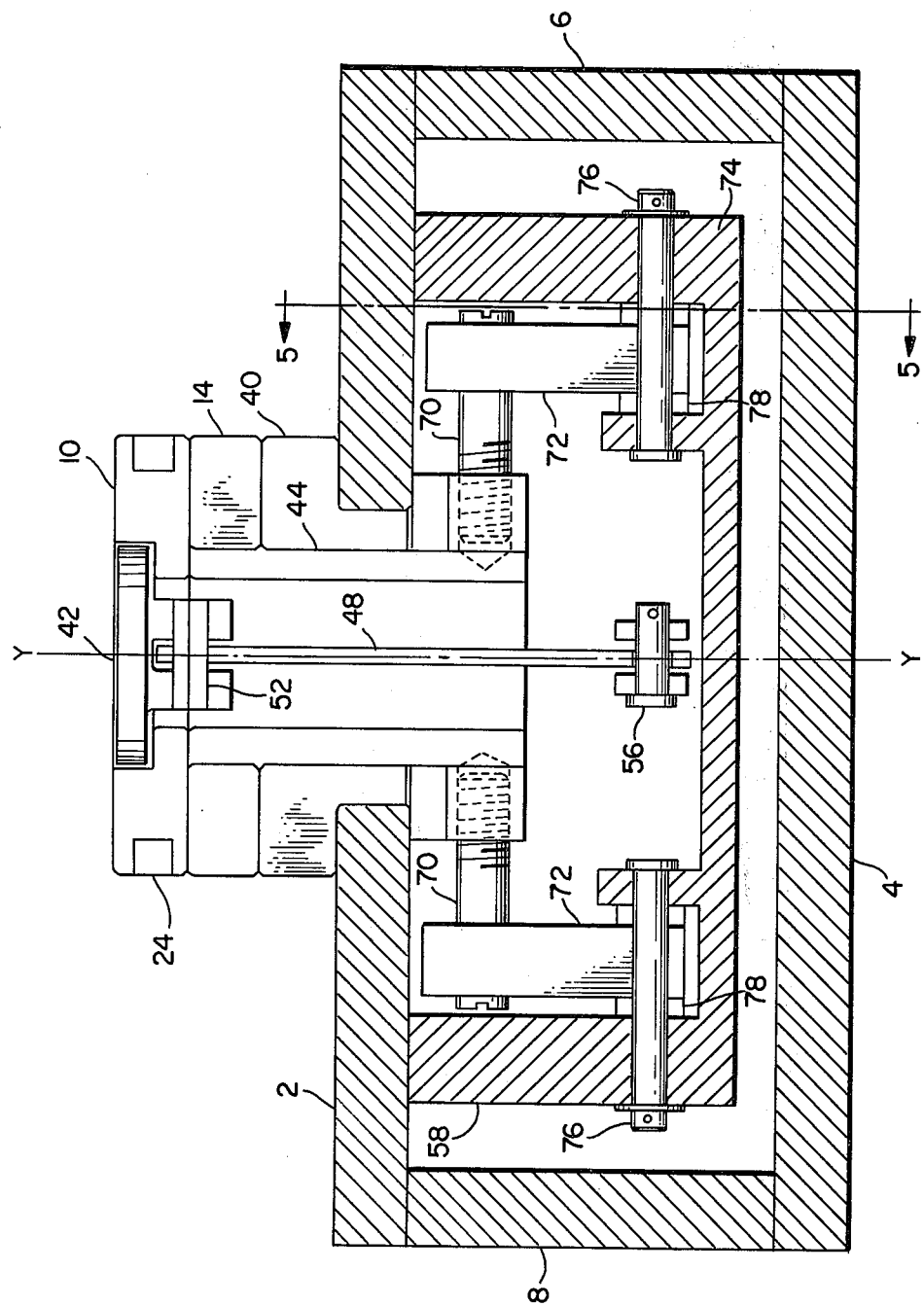
FIG. 4 is a partially sectioned left end view, relative to FIG. 2, showing the internal features of the invention.

With reference first to FIG. 1, the mechanism of the invention which will be hereinafter described is contained in a generally rectangular shaped stationary housing or case designated by the numeral 1 and having a base plate 2, a bottom plate 4 parallel to base plate 2 and a pair of parallel end plates 6 and 8. Base plate 2 serves as a cover for the housing.

A sole plate 10 is hinged through a hinge pin 12 to a pivot plate 14. Pivot plate 14 is journaled in base plate 2 through a bearing assembly designated by the numeral 15 so that sole plate 10 and pivot plate 14 are displaceable about an axis Y-Y normal to the parallel planes of plates 2, 10, and 14, and which axis is shown as vertical in the figure, in response to rightward or leftward applied torsional (twisting) forces.

A retention hinge 16 is secured to one end of base plate 2 through screws 18 extending therethrough and is supported on pivot plate 14 through pivot pin 12. Pivot plate 14 is displaceable about a transverse axis X—X in response to forward or rearward applied bending (pitching) forces. A V-notch member 20, into which the toe of a booted foot of a subject is firmly disposed for purposes to be hereinafter more fully described is arranged normal to and integral with hinge 16.

The opposite end of plate 10 carries a boot heel retainer assembly 22 including a bracket member 23 adjustable along a track 24 carried on the sides of the plate to accommodate variable sized boots, and a heel retaining member 25 is carried on bracket 23.

Thus, plates 2, 10 and 14 provide displaceably mounted means for supporting a suitably booted foot of a subject.

Disposed in base plate 2 are conventional, commercially available type force or pressure indicators 32, 34 and 36, and which indicators indicate the aforenoted applied forces effecting the displacements transmitted by the mechanism of the invention to be described with reference to FIGS. 2, 4 and 5. Indicator 32 indicates a right torsional force, indicator 34 indicates a left torsional force and indicator 36 indicates forward and rearward bending forces.

Pivot plate 14 is supported on a friction adapter 38 as best shown in FIG. 3. Friction adapter 38 is supported on an anti-friction device 39, and which anti-friction device 39 is carried on a specimen plate 41 which is disposed in a track 43 carried on base plate 2 and longitudinally displaceable therealong. Friction adapter 38 cooperates with anti-friction device 39 and specimen plate 41 to simulate a predetermined friction level or to minimize friction to an insignificantly low level for providing accurate force measurements as is desired for the purposes intended and as will be further explained.

In fabricating the invention as so far described, housing 1, sole plate 10, pivot plate 14 and retention hinge 16 may be of aluminum or some other such similar material. Hinge pin 12 may be of steel, while friction adapter 38 and specimen plate 41 may be of a suitable plastic material. Anti-friction device 39 may be of a material compatible with the purposes intended and with reference hereinafter to FIG. 3. Track 43 may be of aluminum, steel or plastic as may be desired for a particular application. Bearing assembly 15 may be of a suitable self-lubricating plastic such as that marketed under the trade name Delrin by the Dupont Corporation.

Reference will now be made to FIGS. 2, 4, 5 and 6 wherein the mechanism for accomplishing the purposes of the invention is shown in substantial detail. A steel ring 46 is suitably secured to a hollow shaft 44. Pivot plate 14 is secured to shaft 44 through a set screw 45. Sole plate 10 is restrained from displacement about hinge pin 12 by a steel link 48 extending through shaft 44. Link 48 is universally joined to sole plate 10 through a washer and pin assembly 52, cap 42 and bearing 50. Shaft 44 is journaled in base plate 2 through bearing assembly 15 including bearings 15A and 15B. Link 48 is restrained tensionally by a leverage system including lever 54, cotter pin and washer assembly 56, post 58 and cotter pin and washer assembly 60 operating against a conventional type hydraulic diaphragm bellows or cylinder designated by the numeral 62.

Diaphragm 62, affected by the aforenoted displacement of sole plate 10 applied through the heretofore described leverage system, transmits the displacement through a closed system including a conventional type hydraulic manifold 66 containing a suitable hydraulic fluid. The fluid is forced through a tube or conduit 68 which may be of copper or the like to indicator 36 shown in FIGS. 1 and 2, whereby the magnitudes of the bending forces which may be applied in either forward or rearward directions, are indicated.

Ring 46 transmits the aforenoted torsional (twisting) displacements of sole plate 10 and pivot plate 14 about axis Y—Y shown in FIGS. 1, 2, 4 and 5 in either rightward or leftward directions to torque arm pins 70 as best shown in FIG. 4. With continued reference to FIG. 4, torque arm pins 70, in turn, apply the displacements through the linkage system including levers 72, yoke support means 74, cotter pin and washer assemblies 76 and spacer washers 78. The linkage system operates against conventional hydraulic cylinders (not shown) such as 62. The torsional displacements are transmitted through closed loop hydraulic systems (not shown) including manifolds such as 66 and conduits such as 68 as described above, and the magnitudes of the forces effecting the displacements are indicated by indicators 32 or 34, as the case may be.

Adjustments for backlash or calibration of the bellows assemblies are effected through an arrangement including set screws 80 and lock nuts 82 as is well known to those skilled in the art and best shown in FIGS. 2 and 5.

It is readily recognized that when a subject combines a forward or rearward bending (pitching) force with a rightward or leftward torsional (twisting) force, such as is within the concern of the invention, there will be a frictional resistance to displacement at the forward end of pivot plate 14, i.e. the end near transverse axis X—X. This is similar to the reaction of ski bindings in snow skiing. Friction adapter 38 and anti-friction device 39, as best shown in FIG. 3, are employed to specifically either simulate the friction involved in a skiing situation or to merely minimize this friction to an insignificantly low level for accurately measuring the force capabilities of the subject as heretofore noted. In the specific case of a skier establishing a ski binding retention index for the purposes of determining an optimum binding adjustment, friction adapter 38 would be of a plastic material simulating that of a typical ski boot sole. Antifriction device 39 would be a commercially available self-lubricating material such as marketed by the Dupont Co. under the trade name Teflon. However, through the use of specimen plate 41 and track 43 heretofore structurally described, variations in the location of the friction adapter and the antifriction device are possible for a variety of applications as will now be understood by those skilled in the art.

In this connection it is to be noted that the device of the invention specifically measures the net torsional (twisting) force applied. That is, the gross force is diminished by the friction resistance of the described anti-friction arrangement so that the net torsional force is indicated on the appropriate indicators. This is necessary for the application of the system in establishing an optimum ski binding adjustment as will be hereinafter discussed.

UTILIZATION OF THE INVENTION

In utilizing the invention heretore described a subject places a suitably booted foot on sole plate 10 so that the toe of the boot fits securely into V-notch 20 and the heel thereof is retained by retainer assembly 22.

Application of a forward bending or pitching force to the lower extremity or leg carrying the booted foot displaces the sole plate about transverse axis X—X. Application of either a rightward or leftward torsional (twisting) force to said lower extremity displaces the sole plate and pivot plate about vertical axis Y—Y.

Through the linkage arrangement and hydraulic systems heretofore described the applied forces effecting said displacements are indicated on the appropriate indicators 32, 34 or 36 as the case may be.

In order to measure the rearward bending force, the subject disposes the heel of the boot in V-notch 20 and utilizes heel retainer assembly 22 as a toe retainer, whereupon the subject bends the lower extremity rearward to apply the required force which is also indicated on indicator 36.

Measurement of the torsional and bending capabilities of the other lower extremity or leg of the subject may be likewise accomplished.

The device of the invention as described may be used as an instrument whereby a skier obtains indices for adjusting ski boot bindings such as described in the aforementioned patents i.e., obtains ski binding retention indicies. Thus, the skier may obtain a "torsional ski binding retention index" for each leg and in each direction, i.e. rightward and leftward and a "bending ski binding retention index" for each leg and in each direction i.e. forward and rearward. Indices so obtained may be calibrated so that the lowest indices consistent with significant discomfort or pain are used for binding adjustment purposes. In this connection it is noted that the torsional indices so calibrated are always a function of the torsional or twisting force on the leg irrespective of the position of the leg with respect to axis Y—Y.

Figure 7:
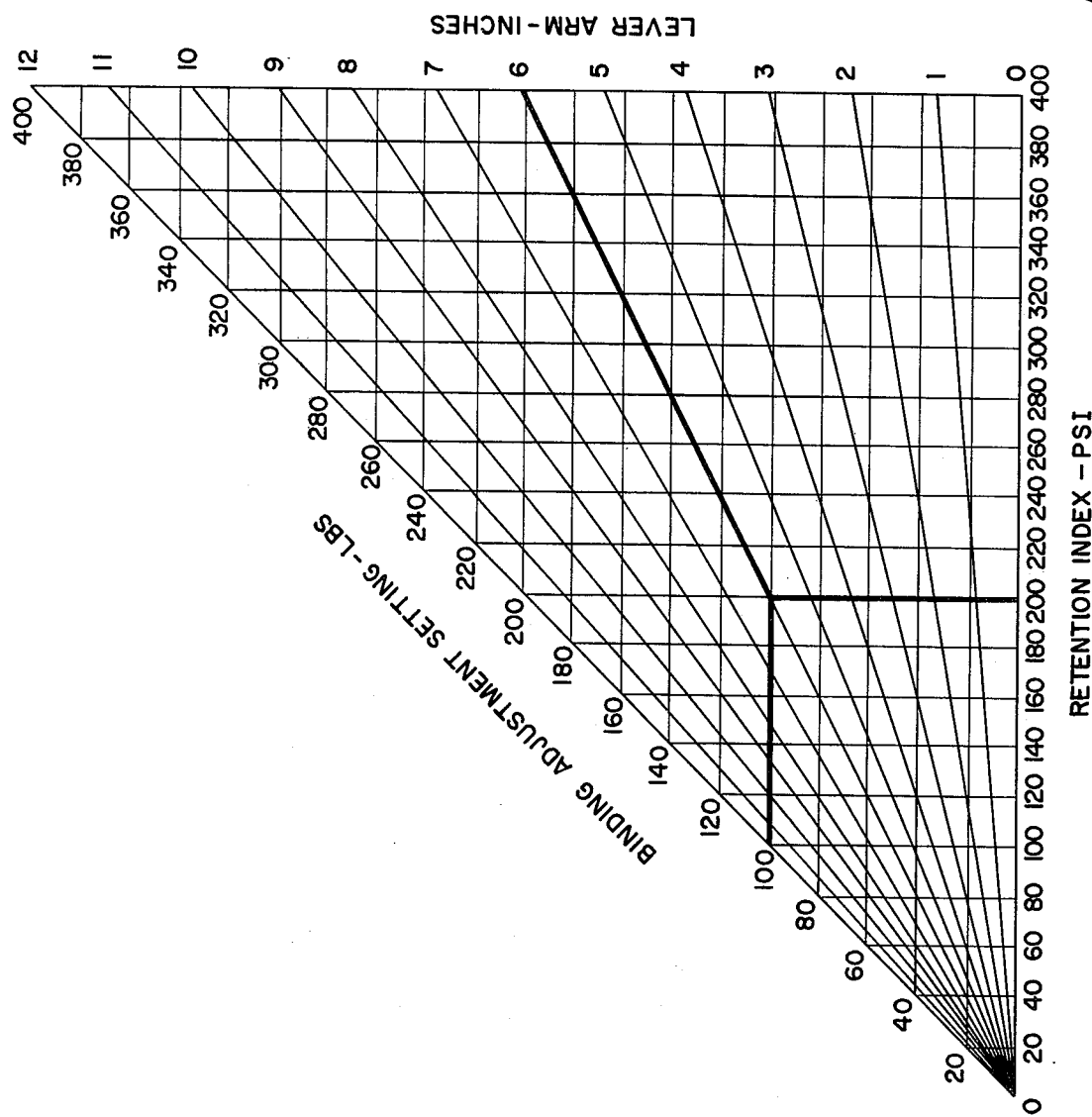
FIG. 7 is a graphical representation showing a ski binding adjustment chart for utilizing measurements made in accordance with the invention.

With reference now to FIG. 7, the graph shown therein is illustrative of how the measurements made as aforenoted may be used for adjusting releaseable ski bindings. The ski binding retention index may be measured as noted and indicated in pounds of force, or pounds per square inch of pressure (as shown) by indicators 32, 34 and 36, and which index is plotted along the abscissa of the graph. The adjustment member of typical releasable ski bindings includes a lever or the like and the length of the lever arm is plotted along the ordinate of the graph. A family of curves is thus provided in accordance with the lever arm of the particular ski binding and the measured retention index (right or left torsional and forward or rearward bending). The family of curves is then used to determine the appropriate binding adjustment setting in pounds. Thus, for a retention index of two hundred PSI and a binding lever arm of six inches, the binding would be adjusted for a one hundred pound retaining force as shown by the heavy lines on the graph.

The retention indices so provided are measures of the capability of the skier to load the ski bindings for skiing within the threshold of significant discomfort or pain as heretofore noted. Further, since controlled skiing does not require the loads to be in excess of ones individual capabilities, the optimum level of the bindings would be at the threshold of this discomfort or pain, or, in other words, proportional to the indices measured, customized to the individual skier.

It will now be seen from the aforenoted description of the invention that a device and method have been provided for establishing direct calibration indices for the lower extremities of a human body. These indices may be correlated for a variety of purposes desired. Although the invention has been specifically described in relation to correlating such indices for the adjustment of releasable ski bindings, it will now be apparent that other correlations will be useful as well. For purposes of illustration only, the strength of the legs after an accident or illness and their relative healing progress could very well be measured in accordance with the invention by practitioners of the medical arts. Therefore, although but a single embodiment of the invention has been described in detail, it is to be expressly understood that the invention is not limited thereto. Various changes may also be made in the design and arrangement of the elements of the apparatus and the steps of the method described without departing from the spirit and scope of the invention as the same will now be understood by those skilled in the art.

What is claimed is:

1. Apparatus for measuring and indicating forces applied to the lower extremities of a human body comprising:
   displaceably mounted means for supporting a suitably booted foot of a subject including means for retaining the toe of the booted foot and means for retaining the heel of the booted foot, and the displaceably mounted means displaced in response to forces applied to a lower extremity carrying the booted foot;
   the displaceably mounted means including a first member, a second member and a third member for supporting the booted foot, the first, second and third members being in parallel planes spaced one above the other;
   the third member displaceably mounted to the second member for displacement about an axis transverse to the parallel planes and near the means for retaining the toe of the booted foot in response to a bending force applied to the lower extremity carrying the booted foot;
   the second member displaceably mounted to the first member for displacement of the second and third members about an axis normal to the parallel planes and intermediate the means for retaining the toe of the booted foot and the means for retaining the heel of the booted foot in response to a torsional force applied to the lower extremity carrying the booted foot;
   friction adapting means disposed intermediate the first and second members and near the transverse axis for providing a predetermined friction characteristic upon combined application of the bending and torsional forces, and including a friction device carried by the first member, a friction adapter disposed intermediate the friction device and the second member, and the friction device and friction adapter cooperating to provide the predetermined friction characteristic;
   means connected to the displaceably mounted means for transmitting the displacements thereof;
   sensing means connected to the displacement transmitting means for sensing the transmitted displacements; and
   means connected to the sensing means and responsive to the sensed displacements for measuring and indicating the applied forces.

2. Apparatus as described by claim 1, including:
   a housing for housing the displacement transmitting means and the sensing means;
   the first member being a cover for the housing; and
   the measuring and indicating means being carried by the first member.

3. Apparatus as described by claim 1, including:
   the means for retaining the toe of the booted foot supported by the second and third members; and
   the means for retaining the heel of the booted foot supported by the third member.

4. Apparatus as described by claim 3, wherein:
   the third member has opposite edges which carry tracks extending longitudinally therealong; and
   the heel retaining means is supported in the tracks and adjustable therealong for accommodating various sized boots.

5. Apparatus as described by claim 1, wherein the friction device includes:
   a track supported by the first member;
   first means carried in the track and longitudinally displaceable therealong; and
   second means supported by the first means intermediate said first means and the friction adapter.

6. A method for measuring and indicating forces applied to the lower extremities of a human body, comprising:
   providing means for supporting a suitably booted foot of a subject and displaceably mounting the supporting means including providing a first member, providing a second member, providing a third member for supporting the booted foot, displaceably mounting the third member to the second member and displaceably mounting the second member to the first member, the first, second and third members being in parallel planes spaced one above the other;
   supporting and retaining the booted foot on the supporting means including supporting the booted foot on the third member and retaining the toe and the heel of the booted foot on the third member;
   applying a force to a lower extremity carrying the supported and retained booted foot for displacing the supporting means including applying a forward bending force to the lower extremity for displacing the third member about an axis near the retained toe of the booted foot and transverse to the parallel planes of the first, second and third members, and sequentially applying rightward and leftward torsional forces to the lower extremity for displacing the second and third members about an axis intermediate the retained toe and heel of the booted foot and normal to the parallel planes.
   sensing the displacements; and
   utilizing the sensed displacements for measuring and indicating the applied forces.

7. A method as described by claim 6, further including:
   correlating the measured and indicated force in accordance with predetermined parameters.

8. A method as described by claim 6, wherein applying a force to that lower extremity carrying the disposed and retained booted foot for displacing the supporting means includes:
   applying a rearward bending force to the lower extremity for displacing the third member about the transverse axis.

9. A method as described by claim 6, further including:
   providing a predetermined friction characteristic upon applying the bending and torsional forces in combination.

10. A method as described in claim 9, wherein providing a predetermined friction characteristic upon applying the bending and torsional forces in combination includes:
  disposing friction adapting means intermediate the first and second members and near the transverse axis.

11. A method as described by claim 6, wherein applying a force to that lower extremity carrying the disposed and retained foot for displacing the supporting means includes:
  applying the force within the threshold of significant discomfort and pain of the subject.

12. A method as described by claim 6, wherein applying a force to that lower extremity carrying the disposed and retained booted foot for displacing the supporting means includes:
  the subject applying the force through his own muscular strength.

13. Apparatus for measuring and indicating a torque and bending moment applied to the lower extremities of a human body, comprising:
  means for supporting a suitably booted foot of a subject, said means being mounted for displacement about a pair of spaced predetermined axes;
  means for retaining the heel of the booted foot and means for retaining the toe of the booted foot on the supporting means;
  the supporting means displaced in response to a bending moment applied to a lower extremity carrying the booted foot about one of the predetermined axes near the toe retaining means and transverse to the plane of the displaceably mounted means, and displaced in response to a torque applied to the lower extremity carrying the booted foot about the other of the predetermined axes intermediate the toe and heel retaining means and normal to the plane of the supporting means; and
  means connected to the supporting means and responsive to the displacements thereof for measuring and indicating the applied torque and bending moment.

14. A method for measuring and indicating a torque and bending moment applied to the lower extremities of a human body, comprising:
  providing means for supporting a suitably booted foot of a subject;
  mounting the supporting means for displacement about a pair of spaced predetermined axes;
  supporting the booted foot on the supporting means;
  arranging means with the supporting means for retaining the heel of the booted foot and retaining the toe of the booted foot on the supporting means;
  applying a bending moment to a lower extremity carrying the booted foot for displacing the supporting means about one of the predetermined axes near the retained toe of the booted foot and transverse to the plane of the supporting means;
  applying a torque to the lower extremity carrying the booted foot for displacing the supporting means about the other of the predetermined axes intermediate the retained toe and heel of the booted foot and normal to the plane of the supporting means;
  sensing the displacements of the supporting means; and
  utilizing the sensed displacements for measuring and indicating the applied torque and bending moment.

* * * * *